US 8,552,246 B2

(12) United States Patent
Kuznicki et al.

(10) Patent No.: US 8,552,246 B2
(45) Date of Patent: Oct. 8, 2013

(54) REMOVAL OF CARBON DIOXIDE FROM PARAFFINS

(75) Inventors: Steven M. Kuznicki, Edmonton (CA); Alejandro Anson, Zaragoza (ES); Christopher C. H. Lin, Edmonton (CA); Patricio S. Herrera, Calgary (CA)

(73) Assignee: The Governors of the University of Alberta, Alberta (CA)

( * ) Notice: Subject to any disclaimer, the term of this patent is extended or adjusted under 35 U.S.C. 154(b) by 806 days.

(21) Appl. No.: 12/660,557

(22) Filed: Mar. 1, 2010

(65) Prior Publication Data

US 2010/0228069 A1  Sep. 9, 2010

(30) Foreign Application Priority Data

Mar. 5, 2009 (CA) ................................. 2657127

(51) Int. Cl.
*C07C 7/13* (2006.01)

(52) U.S. Cl.
USPC ........... 585/824; 585/802; 585/820; 585/823; 95/95; 95/116; 95/139

(58) Field of Classification Search
USPC .......... 585/802, 820, 822, 823, 824; 502/407, 502/411
See application file for complete search history.

(56) References Cited

U.S. PATENT DOCUMENTS

| | | | |
|---|---|---|---|
| 2,860,030 A | 11/1958 | Goldstrap et al. | |
| 3,176,445 A | 4/1965 | Collins et al. | |
| 3,430,418 A | 3/1969 | Wagner | |
| 3,751,878 A | 8/1973 | Collins | |
| 4,589,888 A | 5/1986 | Hiscock et al. | |
| 4,775,396 A | 10/1988 | Rastelli et al. | |
| 4,853,202 A * | 8/1989 | Kuznicki | 423/326 |
| 4,938,939 A | 7/1990 | Kuznicki | |
| 5,011,591 A | 4/1991 | Kuznicki | |
| 5,208,006 A | 5/1993 | Kuznicki et al. | |
| 5,244,650 A | 9/1993 | Kuznicki et al. | |
| 5,414,190 A * | 5/1995 | Forg et al. | 585/802 |
| 5,531,808 A | 7/1996 | Ojo et al. | |
| 5,587,003 A | 12/1996 | Bulow et al. | |
| 5,779,767 A | 7/1998 | Golden et al. | |
| 5,906,954 A | 5/1999 | Koermer | |
| 5,938,819 A | 8/1999 | Seery | |
| 5,989,316 A | 11/1999 | Kuznicki et al. | |

(Continued)

FOREIGN PATENT DOCUMENTS

| CA | 2618267 A1 | 7/2009 |
|---|---|---|
| EP | 173501 A2 | 3/1986 |

OTHER PUBLICATIONS

Georg Hammer, Torsten Lubcke, Roland Kettner, Mark R. Pillarella, Herta Recknagel, Axel Commichau, Hans-Joachim Neumann, and Barbara Paczynska-Lahme, "Natural Gas," Jul. 15, 2006, Wiley-VCH, Ullman's Encyclopedia of Industrial Chemistry vol. 23, pp. 740-741.*

(Continued)

*Primary Examiner* — In Suk Bullock
*Assistant Examiner* — Candace R Chouinard
(74) *Attorney, Agent, or Firm* — Kenneth H Johnson

(57) ABSTRACT

ETS-10 titanosilicate materials selectively adsorb carbon dioxide from gaseous mixtures containing carbon dioxide and light paraffins such as methane and ethane.

9 Claims, 1 Drawing Sheet

(56) References Cited

U.S. PATENT DOCUMENTS

| | | | |
|---|---|---|---|
| 6,024,781 | A | 2/2000 | Bulow et al. |
| 6,068,682 | A | 5/2000 | Kuznicki et al. |
| 6,197,092 | B1 | 3/2001 | Butwell et al. |
| 6,293,999 | B1 | 9/2001 | Cheng et al. |
| 6,309,445 | B1 | 10/2001 | Gittleman et al. |
| 6,387,159 | B1 | 5/2002 | Butwell et al. |
| 6,497,750 | B2 | 12/2002 | Butwell et al. |
| 6,517,611 | B1 | 2/2003 | Kuznicki et al. |
| 6,610,124 | B1 | 8/2003 | Dolan et al. |
| 7,314,503 | B2 | 1/2008 | Landrum et al. |
| 2007/0261551 | A1 | 11/2007 | Sawada et al. |

OTHER PUBLICATIONS

Heinz Zimmerman and Roland Walzl, "Ethylene," Apr. 15, 2007, Wiley-VCH, Ullman's Encyclopedia of Industrial Chemistry, pp. 1 and 10.*

Walden L.S. Laukhuf et al, Adsorption of carbon dioxide, acetylene, ethane and propylene . . . , Jour. of Chem. and Eng. Data., Jan. 1969, vol. 14, No. 1, p. 48-51.

R. Reich et al, Adsorption of methane, ethane and ethylene gases . . . , Ind. Eng. Chem. Process Des. Dev., 1980, vol. 19, p. 336-344.

V. R. Choudhary et al, Sorption of isotherms of methane, ethane, ethylene, and carbon dioxide . . . , Langmuir, 1996, vol. 12, p. 980-986.

V.R. Choudhary et al, Adsorption of methane, ethane, ethylene, and carbon dioxide on silicalite-1, Zeolites 17, p. 501-507, Elserier Science Inc. 1996, NY, NY.

Y. He et al, Heats of adsorption heterogeneity for methane, ethane, and carbon dioxide in MCM-41, Langmuir,2006, vol. 22, p. 1150-1155.

V.R. Choudhary et al, Sorption of isotherms of methane, ethane, ethene and carbon dioxide . . . J. Chem Soc., Faraday Trans,1995, vol. 91 No. 17 p. 2935-2944.

D.W. Breck, Zeolite molecular sieves: structures, chemistry, and use, John Wiley and Sons, London, 1974, Chap. 8, p. 593-699.

N.A. Al-Baghli et al, adsorption of methane, ethane, and ethylene on titanosilicate ETS-10 zeolite, J. Chem. Eng. Data, 2005, vol. 50, p. 843-8-48.

N.A. Al-Baghli et al, Binary and ternary adsorption of methane, ethane, and ethylene on titanosilicate ETS-10-zeolite, J. Chem. Eng. Data, 2006, vol. 51, p. 248-254.

Kirk-Othmer Encyclopedia of Chemical Technology, John Wiley & Sons, 2003, on line pub. up dated Jan. 8, 2010 vol. 1 p. 636-647.

* cited by examiner

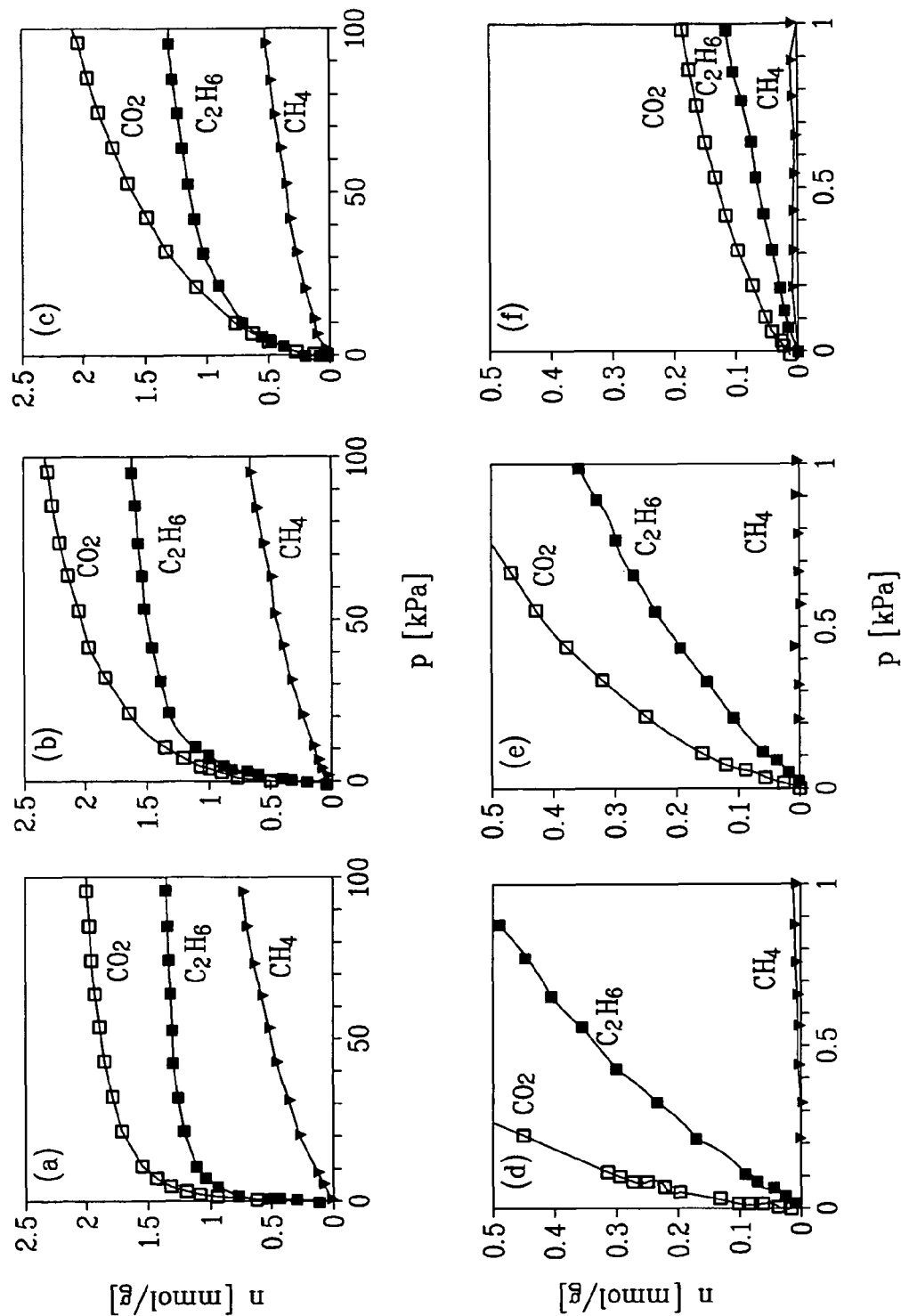

REMOVAL OF CARBON DIOXIDE FROM PARAFFINS

FIELD OF THE INVENTION

The current invention is directed to the use of solid adsorbent materials which adsorb carbon dioxide from a mixture which comprises paraffins and carbon dioxide. More specifically, as-prepared or modified ETS-10 titanosilicate materials are used to selectively adsorb carbon dioxide from gaseous mixtures containing carbon dioxide and light paraffins such as methane or ethane.

BACKGROUND OF THE INVENTION

The separation of carbon dioxide ($CO_2$) from natural gas or NGLs is an important step in the petrochemicals industry. Carbon dioxide contamination can lower the heating value of methane and increase transportation costs. Alternatively, carbon dioxide contamination of $C_2$ or $C_3$ paraffin streams can lead to the formation of impurities during hydrocarbon cracking processes. Processes which sequester $CO_2$ product streams may also be utilized in enhanced oil recovery processes.

The use of liquid extraction to scrub acid gases such as carbon dioxide ($CO_2$) from natural gas or NGL streams is well known and typically employs an aqueous amine solvent system. Amine scrubbers work best when the $CO_2$ levels in a hydrocarbon inlet stream are relatively low. The amine components typically employed vary widely, but the use of alkanolamines is well established. Despite their effectiveness, amine based scrubbers can be costly and difficult to operate. For example, solvent contamination is often a problem. In addition, the use of an aqueous scrubber system may cause natural gas streams or hydrocarbons to become saturated with water. Removal of water from hydrocarbon gas streams involves further purification steps (i.e. absorption by glycol systems) and further cost is added to the overall process.

In addition to the above liquid extraction systems, solid adsorbents have been explored for adsorptive uptake of carbon dioxide ($CO_2$), ethane ($C_2H_6$), and methane ($CH_4$). For example, the adsorption capacities of activated carbon materials at gas pressures below 1 bar typically decrease in the order $C_2H_6 > CO_2 > CH_4$ (see FIG. 1 of the article by Laukhuf, W. L. S and Plank, C. A. in the *Journal of Chemical Engineering Data*, 1969, 14(1), p 48.; also see Reich, R.; Ziegler, W. T. in *Industrial and Engineering Process Design and Development*, 1980, 19, p 336). Activated carbon materials are thus selective towards ethane (and not carbon dioxide) and are not directly useful for reducing $CO_2$ levels in light paraffin streams. Similarly, some molecular sieves adsorb carbon dioxide less strongly than ethane, and follow the uptake capacity sequence $C_2H_6 > CO_2 > CH_4$. This is the case for ALPO-5 (see FIG. 2 in the article by Choudhary and Mayadevi in *Langmuir*, 1996, 12, p 980), SAPO-5 (see FIG. 3 in the article by Choudhary and Mayadevi in *Langmuir*, 1996, 12, p 980), and silicalite-1 (see FIG. 1 in the article by Choudhary and Mayadevi in *Zeolites* 1996, 17, p 501). In contrast, templated, high silica zeolites usually follow the capacity sequence $CO_2 > C_2H_6 > CH_4$, but present very low $CO_2/C_2H_6$ selectivity, as it is observed for ZSM-5 (see FIG. 4 of the article by He, Y and Seaton, N. A. in *Langmuir*, 2006, 22, p 1150). These adsorbents cannot be used for a pressure swing adsorption (PSA) separation of $CO_2$ from ethane, but with their nearly linear $CO_2$ isotherms, have good opportunities for $CO_2/CH_4$ pressure swing adsorption separations. Product recovery would suffer, however, due to the adsorbent's significant $CH_4$ capacity.

Classical aluminosilicate materials and particularly their uses in the sequestration of $CO_2$ from feed gases comprising hydrocarbons are well represented in both the patent and academic literature. For example, aluminosilicate zeolites such as 13X are known to selectively adsorb carbon dioxide over ethane and methane (see FIG. 2 of the article by Choudhary, V. R.; Mayadevi, S.; Singh, A. P. in the *Journal of the Chemical Society, Faraday Transactions*, 1995, 91(17), p 2935). Similar trends have been found for NaY, Na-mordenite and 4A zeolite materials (see Breck, D. W. in *Zeolite Molecular Sieves: Structure, Chemistry and Use*. Wiley-Interscience Publication, John Wiley and Sons, London, 1974). However, the shape of the $CO_2$ isotherms for 13X zeolites can vary over a wide range and are generally too steep for normal PSA processes. These materials may be more suitable for thermal swing adsorption processes.

U.S. Pat. No. 3,751,878 describes a zeolite molecular sieve for adsorbing carbon dioxide selectively from a gaseous mixture also containing methane and hydrogen. The zeolite used was a traditional porous aluminosilicate material. Several synthetic or naturally occurring zeolites were disclosed including types A, T, X, Y, S, and Z (also see: U.S. Pat. No. 3,176,445 and the references cited therein).

EP 0173501 A2 teaches the use of a faujasite type zeolite which has been ion exchanged with alkali or alkali earth metals, to achieve separation of $CO_2$ from non-acidic gases. Non-acidic gases include carbon monoxide, nitrogen and methane. The faujasite materials within the scope of the patent were zeolites X and Y, provided they had a silicon to aluminum atomic ratio of 1.2 to 3.

U.S. Pat. No. 4,775,396 teaches selective adsorption of $CO_2$ from methane, hydrogen or nitrogen using pressure swing adsorption. The adsorbent used was a zeolite X or Y material which was modified by cations selected from the group consisting of zinc, rare earth metals, $H^+$ or $NH_4^+$ cations. U.S. Pat. No. 5,531,808 teaches a similar separation employing zeolite X, but with a silicon to aluminum atomic ratio of not greater than 1.15. With this Si:Al ratio, the adsorption of $CO_2$ during pressure swing processes can be carried out at above 20° C. Further modifications to zeolite X materials for use in $CO_2$ sequestration is the subject matter of U.S. Pat. No. 6,309,445. The patent teaches the use of a type X zeolite which has a silicon to aluminum ratio of less than 1.15 and has at least 75% of its exchangeable cations as potassium ions.

The use of clinoptilolite to selectively adsorb carbon dioxide from methane and other non-polar gases is taught in U.S. Pat. No. 5,587,003. Bulk separation of $CO_2$ from methane by pressure swing adsorption where the adsorbent is naturally occurring sodium rich clinoptilolite is the subject matter of U.S. Pat. No. 5,938,819.

The adsorption of $CO_2$, water, oxides of nitrogen and preferably acetylene from a feed gas can be affected by a mixture of zeolite and alumina as taught in U.S. Pat. No. 5,779,767. Traditional aluminosilicate zeolites are used to prepare a "fixture" with alumina.

The separation of carbon dioxide from $C_1$ to $C_6$ hydrocarbons using a pressure swing or temperature swing process (from approximately −50° C. to 200° C.) is taught in U.S. Pat. No. 6,024,781. The patent uses zeolite A having exchangeable cations 40-90% $Na^+$, 10-50% $K^+$, and 0-10% other cations, as the adsorbent material. Removal of $CO_2$ from acetylene is exemplified.

The zeolites discussed above are natural or synthetic aluminosilicate zeolite materials. Alternatively, Engelhard has developed a new type of zeolite material comprising a family of titanosilicate zeolite materials. Titanosilicate materials are known to be useful in the adsorptive separation of nitrogen from methane (see U.S. Pat. Nos. 6,068,682 and 5,989,316). Some titanosilicate materials, such as ETS-4 and CTS-1 have pore sizes in the range of 4 and 3 Å, respectively (see U.S. Pat. Nos. 4,938,939; 5,011,591 and 6,517,611) and are commercially available from Engelhard as Molecular Gate® materials. These Molecular Gate® materials have also found use as adsorbents in pressure swing adsorption processes which separate nitrogen and/or carbon dioxide from natural gas. For example, U.S. Pat. No. 6,610,124 teaches that a cation-exchanged ETS-4 material, preferably Ba-ETS-4 may be used in an adsorption bed to selectively remove nitrogen and carbon dioxide from the $C_1$ and $C_2$ components of a natural gas feed stream. The patent also teaches the use of CTS-1 to effect similar separations. Molecular Gate® materials such as ETS-4 and CTS-1 exclude carbon dioxide on the basis of size, and hence facilitate a kinetic type separation. CTS-1 titanosilicate adsorbents have even been used in combination with traditional amine solvent scrubbers to reduce the $CO_2$ levels in natural gas (see U.S. Pat. No. 7,314,503 to Syntroleum).

In contrast, ETS-10 titanosilicate materials, also developed by Engelhard (see U.S. Pat. No. 5,011,591), have large pore diameters of about 8 Å and are not expected to act as Molecular Gate® materials. Despite this, ETS-10 materials have been used to separate ethylene from mixtures of ethylene and paraffins of the same carbon number (see for example co-pending Canadian Patent application No. 2,618,267 and Al-Baghli and Loughlin in *J. Chem.* Eng. Data 2006, v51, p 248). The use of ETS-10 materials in the selective uptake of carbon dioxide from light paraffins has not been explored. ETS-10 materials have better thermal stability than some of their Molecular Gate® counterparts (i.e. ETS-4), and may prove to be better suited for higher temperature applications.

SUMMARY OF THE INVENTION

We have found that a thermodynamic separation of oxygenated carbon species from natural gas or light paraffins can be effected by use of a large pore titanosilicate material. Both unmodified and modified versions of so-called ETS-10 zeolites are appropriate for use in the current invention.

In addition we have found that the shape of the adsorption isotherms and the selectivity of the adsorption for $CO_2$, methane, and ethane on ETS-10 can be modified by ion-exchange of the ETS-10 material.

In an aspect of the invention, an ETS-10 zeolite material is provided for use as an adsorbent in the separation of carbon dioxide from light paraffins.

In another embodiment of the invention, cationically modified ETS-10 zeolites are provided which have improved applicability to pressure swing adsorption processes which separate carbon dioxide from natural gas or light paraffins.

Provided is a process for increasing the proportion of paraffins in a mixture containing carbon dioxide and at least one paraffin, where the process includes passing the mixture over an adsorbent which contains as a main component, an ETS-10 zeolite material.

In an aspect of the invention, carbon dioxide is separated from methane, ethane or a mixture thereof, using a modified and/or unmodified ETS-10 zeolite.

In some aspects of the invention an as-prepared Na-ETS-10 zeolite which has been modified with one or more than one mono-, di- or tri-valent metal cation, a proton ($H^+$) or mixtures thereof is used as an adsorbent material.

The invention provides a pressure swing adsorption process employing a step in which a mixture of carbon dioxide and paraffins are passed over an ETS-10 zeolite material which selectively uptakes carbon dioxide.

In another aspect of the invention, a pressure swing adsorption process increases the proportion of light paraffins in a gaseous mixture of light paraffins and carbon dioxide, provided that the process includes at least the following steps:
  i) passing the mixture through an adsorption bed containing an adsorbent comprising an as-prepared and/or modified ETS-10 zeolite at a pressure at which the adsorbent selectively adsorbs carbon dioxide from the gaseous mixture to provide a stream enriched in at least one light paraffin; and
  ii) reducing the pressure in the adsorption bed to a pressure at which the adsorbent releases adsorbed carbon dioxide in order to provide a stream enriched in carbon dioxide.

In another aspect of the invention an integrated process is provided which comprises:
  i) an adsorption process upstream of a hydrocarbons cracking unit, where the adsorption process comprises passing a gaseous mixture which minimally contains carbon dioxide and at least one paraffin, over an adsorbent comprising an as-prepared and/or modified ETS-10 zeolite to provide a product stream enriched in at least one paraffin; and
  ii) cracking at least one paraffin in the product stream in the hydrocarbons cracking unit.

Provided is a process for increasing the proportion of at least one paraffin in a mixture comprising carbon dioxide and the at least one paraffin, wherein the process comprises at least the following steps:
  i) passing the mixture over an adsorbent, wherein the adsorbent comprises an as-prepared and/or modified ETS-10 zeolite and wherein the adsorbent selectively adsorbs carbon dioxide from the mixture; and
  ii) passing the mixture through an amine based liquid extraction unit, wherein the extraction unit selectively extracts carbon dioxide from the mixture.

In the present invention, an adsorbent comprising an as-prepared ETS-10 zeolite and/or a modified ETS-10 zeolite is used to selectively adsorb carbon dioxide from a mixture which minimally contains carbon dioxide and at least one paraffin.

BRIEF DESCRIPTION OF THE DRAWINGS

FIG. 1 shows carbon dioxide, ethane, and methane adsorption isotherms at 25° C. for: a) Na-ETS-10, b) Ba-ETS-10, c) Ba/H-ETS-10 (1 meq Ba) up to 100 kPa and d) Na-ETS-10, e) Ba-ETS-10, f) Ba/H-ETS-10 (1 meq Ba) up to 1 kPa.

DETAILED DESCRIPTION

The present invention relates to the use of adsorbents comprising large pore titanium silicate molecular sieves for the separation of carbon dioxide ($CO_2$) from light paraffins.

The current invention contemplates the use of unmodified (i.e. "as-prepared" ETS-10) or modified ETS-10 materials. ETS-10 is a large-pored titanosilicate molecular sieve with an average pore size of about 0.8 nm. Carbon dioxide and light paraffins are all small enough to enter the pores of ETS-10 without constrictions, and no size-selectivity effects are expected for the separation of carbon dioxide from paraffins such as methane or ethane. Without wishing to be bound by theory, modification of the shape of adsorption isotherms, and adsorptive selectivity for carbon dioxide and paraffins such as methane and ethane is altered in ETS-10 zeolites by controlling the strength (i.e. affinity) of the adsorption sites (rather than controlling pore sizes) through modification.

The term "paraffin" as used herein refers to any fully saturated hydrocarbons and includes but is not limited to methane, ethane, propane, n-butane, n-pentane and the like, with methane and ethane being preferred. "Light paraffins" as the term is used herein refers to any fully saturated hydrocarbons which are gaseous under standard temperature and pressure conditions (i.e. 0° C. or 273 K; standard pressure is 1 atmosphere).

In the current invention the paraffins and carbon dioxide are preferably gaseous under the process conditions.

In the current invention, carbon dioxide may be selectively adsorbed from a mixture in which one paraffin type predominates. In one aspect of the invention the paraffin portion of a mixture comprising carbon dioxide and at least one paraffin will be composed of at least 50 weight percent (wt %) of methane or at least 50 wt % of ethane.

In another aspect of the invention the paraffin portion of a mixture comprising carbon dioxide and at least one paraffin will be composed of at least 75 wt % of methane or at least 75 wt % of ethane. In yet another aspect of the invention the paraffin portion of a mixture comprising carbon dioxide and at least one paraffin will be composed of at least 90 wt % of methane or at least 90 wt % of ethane.

As used herein, the term "modified" encompasses cationic modification and structural modification (or structural variation) of an as-prepared ETS-10 zeolite.

As used herein the term "cationic modifier" represents a cation, typically delivered in the form of a salt or acid, which when added to an unmodified ETS-10 zeolite, provides a modified ETS-10 zeolite through cation exchange reactions.

As used herein the term "structural modifier" represents a compound, which when added to an unmodified ETS-10 zeolite, provides a modified ETS-10 zeolite through substitutions of Ti and/or Si sites or through extraction of a portion of the titanium present. Structural modifiers can also be added during the synthesis of an unmodified ETS-10 to give a modified ETS-10 zeolite.

As used herein, the term "pore diameter" refers to the effective diameter of the largest gas molecule that can be significantly adsorbed by the ETS-10 zeolite materials. This may be similar to, but different from the crystallographically determined pore diameter of the ETS-10 zeolite material.

The terms "ETS-10", "ETS-10 zeolite" or "ETS-10 materials" are used to connote large pore titanosilicates in general and can connote either as-prepared ETS-10 or modified ETS-10 materials.

As used herein terms such as "separate", "separation", "selective removal", "selective adsorption" and the like connote a partial or full separation of at least one component in a gaseous mixture. Hence at least one component may be completely removed or isolated (i.e. purity of 90% or higher) or merely enriched (i.e. the concentration or proportion of a component in a gaseous mixture is increased beyond its initial value) during the process of the current invention. Other terms and phrases such as "enrichment" and "increasing the proportion" respectively, are also meant to connote a partial or full separation of at least one component in a gaseous mixture as will be readily appreciated by a person skilled in the art.

As used herein the term "pressure swing capacity" has its conventional meaning and generally refers to the amount (in millimoles per gram, mmol/g) of gaseous component (i.e. carbon dioxide) that can be adsorbed on and desorbed from an adsorbent, between a first higher pressure and a second lower pressure, respectively. In the current invention, the pressure swing capacity is reported as the amount of a gaseous component that can be adsorbed and/or desorbed over a given pressure range at a given temperature as indicated by an adsorption isotherm. In the present invention, the pressure swing capacity is reported between 1 and 100 kPa. The pressure swing capacity may also be represented as a percentage, or a "working swing capacity", where the pressure swing capacity is normalized with respect to the total adsorption at 100 kPa (i.e. the pressure swing capacity between 0 to 100 kPa). Hence, the working swing capacity, is the pressure swing capacity of from 1 to 100 kPa divided by the total pressure swing capacity from 0 to 100 kPa, as represented in percent form. The working swing capacity is indicative of the shape (i.e. rectangularity) of the adsorption isotherm. It will be obvious to a person skilled in the art, that a "swing capacity" for a temperature range can be similarly defined.

As used herein, the term "stream" has its conventional meaning and refers to liquid or gaseous mixture which can be a feed, product, recycle or waste stream that can be fed to or received from an adsorbent bed in a pressure swing or temperature swing adsorption process.

As used herein, the term "mixture" refers to a liquid or gaseous mixture which minimally contains carbon dioxide and at least one paraffin.

Unmodified or "as-prepared" ETS-10 zeolites which are also herein designated "Na-ETS-10" zeolites, mainly contain $Na^+$ as exchangeable counter-ions but in some cases, depending on preparation conditions, may also contain exchangeable $K^+$ counter-ions. The unmodified titanium silicate molecular sieves (i.e. Na-ETS-10) of the current invention have octahedral titanium sites and tetrahedral silicon sites, providing a structure with an average pore diameter of approximately 8 Å and a titania/silica molar ratio of from 2.5 to 25. A non-limiting description of unmodified ETS-10 zeolites is given in Table 1 of *J. Chem. Eng. Data.* 2005, 50, p 843 by Al-Baghli et al. which is incorporated herein by reference.

The "modified" ETS-10 titanium silicates are derived from "as-prepared" or unmodified ETS-10 zeolites through cation exchange reactions and/or structural exchange reactions. Alternatively, modified ETS-10 zeolites may be obtained by manipulation of the preparative recipe and conditions used for making Na-ETS-10. All such modifications are contemplated by the current invention, provided that the modified ETS-10 zeolite remains selective for the adsorption of carbon dioxide over paraffins.

In the current invention, the terms "modified" or "modified ETS-10 zeolite" connote an Na-ETS-10 zeolite in which at least some of the exchangeable $Na^+$ and/or $K^+$ ions originally present in the zeolite are replaced by other cationic species by cationic exchange reactions. Such modifications are "cationic modification(s)". The terms "modified" or "modified ETS-10 zeolite" also connote a titanium silicate zeolite which differs from an as-prepared Na-ETS-10 zeolite by one or more substitutions at the octahedral titanium sites or the tetrahedral silicon sites (i.e. a structural variant of Na-ETS-10 in which a partial exchange of Ti and/or Si has occurred). Such Ti and/or Si substitutions are structural in nature and for the purposes of the current invention are designated "structural modification(s)". Hence, in the current invention, the terms "modified" or "modified ETS-10 zeolites" includes ETS-10 zeolites that have either or both of:
  i) substitution of exchangeable cations (e.g. $Na^+$ and/or $K^+$ sites);
  ii) substitution at the titanium and/or silicon sites.

By way of non-limiting example, a Na-ETS-10 can be cationically modified by stirring the Na-ETS-10 zeolite with a suitable cation source, to exchange some of the exchangeable cations originally present in the Na-ETS-10.

Structural variations to the Ti or Si sites of Na-ETS-10 can be achieved by modifying or changing the source components used to make the Na-ETS-10. Structural modification can also be achieved though use of exchange reactions where the Ti and/or Si sites of "as-prepared" Na-ETS-10 are substituted by suitable metal species, after the Na-ETS-10 material is isolated. Both types of structural modification are known in the art and are discussed in U.S. Pat. Nos. 5,244,650 and 5,208,006.

Members of the ETS-10 molecular sieve zeolite type, have a crystalline structure and an X-ray powder diffraction pattern with significant lines at or near those disclosed in Table 1 of U.S. Pat. No. 5,011,591, the entirety of which is incorporated herein by reference. By "near" it is meant that the major lines can shift, on modification of Na-ETS-10, by as much as 1 unit or more, but will maintain essentially the same pattern in an X-ray powder diffraction pattern. Hence, modified ETS-10 zeolites will have substantially the same pattern of major lines in an X-ray powder diffraction pattern as unmodified Na-ETS-10.

As-prepared ETS-10 zeolites can be prepared by mixing a source of silica (e.g. silica; silica hydrosol; silica gel; silicic acid; alkoxides of silicon; alkali metal silicates such as but not limited to sodium and potassium silicate; mixtures thereof and the like); a source of trivalent titanium (e.g. $TiCl_3$ etc.); a base such as but not limited to an alkali metal hydroxide (e.g. NaOH, NaOH(aq), KOH, etc.) for controlling the pH of the reaction mixture at from 9.9 to 10.3±0.1; water; and optionally an alkali metal halide (NaCl, NaF, KF etc.) in specific ratios. In an aspect of the invention, Na-ETS-10 is prepared from a reaction mixture having a composition in terms of molar ratios of:

$SiO_2/Ti$=from about 2 to about 20
$H_2O/SiO_2$=from about 2 to about 100
$M_n/SiO_2$=from about 0.1 to about 10

For further suitable, but non-limiting ratios of these source components see Table 2 of U.S. Pat. No. 5,011,591 that is incorporated herein by reference. The mixture is typically heated to a temperature of between 100° C. and 200° C. and stirred for at least 8 hrs. The "as-prepared" Na-ETS-10 zeolite forms as crystals within the reaction mixture. Stirring of the reaction mixture is beneficial but in some cases is optional, especially when using silica gel as the source of silica. The crystals are separated by filtration and optionally washed with water, followed by drying at temperatures of up to about 250° C. for up to about 72 hrs.

In an aspect of the invention, the "as-prepared" or unmodified Na-ETS-10 is a zeolite prepared according to Examples 5, 6, 7 or 9 of U.S. Pat. No. 5,011,591.

In an aspect of the invention, unmodified Na-ETS-10 zeolite is prepared and isolated prior to modification by cation exchange reactions or structural substitution reactions.

Both "as-prepared" and "cationically modified" ETS-10 zeolites have a composition that in some aspects of the invention may be represented by the following formula:

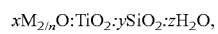

$$xM_{2/n}O:TiO_2:ySiO_2:zH_2O,$$

where M is a mono-, di-, or tri-valent cationic ion, n is the valence of M, x is from 1 to 10, y is from 2.5 to 25, and z is from 0 to 150. In "as-prepared" or unmodified titanium silicate, M is sodium and/or potassium. In cationically modified ETS-10, sodium and/or potassium ions are ion exchanged for at least one cation not originally present in the "as-prepared" or unmodified titanium silicate. Alternatively, in cationically modified ETS-10 zeolites, the $Na^+$ ions can be replaced with $K^+$ ions.

The cation exchange capacity (CEC) is a measure of the exchangeable cations present in an ETS-10 zeolite. It can be measured in SI units as the positive charge (in coulombs) absorbed by the zeolite per unit of mass of the zeolite. It is also conveniently measured in milliequivalence per gram of zeolite (meq/g) or per 100 gram of zeolite (meq/100 g). The cation exchange capacity of the unmodified zeolites is not specifically defined, but in one aspect of the invention the CEC can be at least 50 milliequivalence per 100 g. In another aspect of the invention, the unmodified zeolite can have a CEC of from about 1.0 to about 10 meq/g.

The percentage of ions exchanged during the formation of the cationically modified ETS-10 zeolite is not specifically defined, provided that the adsorbent remains selective for the adsorption of CO2 over paraffins. By way of a non-limiting example, from about 5% to 100% of the exchangeable $Na^+$ and/or $K^+$ ions originally present in the "as-prepared" ETS-10 may be exchanged by cation exchange.

In an aspect of the invention, the amount of cation added to the unmodified ETS-10 can be from about 1% to about 1000% of the cationic exchange capacity of the zeolite, preferably from about 25% to about 250%. One or more than one type of cationic modifier can be added to Na-ETS-10. For example, a first cationic modifier may be added by treating an as-prepared Na-ETS-10 zeolite with a cation in concentrations (meq/g) below the CEC of the zeolite, followed by the addition of a second, third, or fourth etc. cationic modifier to replace some or all of the remaining exchangeable $Na^+$ and $K^+$ sites. Cationic exchange can involve sequential or simultaneous addition of one or more of the same or different cationic modifiers to an unmodified ETS-10 zeolite.

In the current invention, modification can include partial or full replacement of exchangeable $Na^+$ and/or $K^+$ ions for one or more than one mono, di- or tri-valent cation or mixtures thereof. Modification can also include partial or complete replacement of exchangeable $Na^+$ ions for $K^+$ ions.

In an aspect of the invention, the modified ETS-10 zeolite is an "as-prepared" ETS-10 zeolite that has been cation exchanged with a mono, di- or tri-valent cation or mixtures thereof. Either or both of $Na^+$ or $K^+$ may be ion exchanged for a mono-, di- or tri-valent cation.

In an aspect of the invention, the mono-, di- and tri-valent cations are selected from the group 2-4 metals, a proton, ammonium compounds and mixtures thereof. Some specific non-limiting examples of mono-, di, or tri-valent cations that can be used in the current invention include, $Li^+$, $K^+$, $Cs^+$, $Mg^{2+}$, $Ca^{2+}$, $Sr^{2+}$, $Ba^{2+}$, $Sc^{3+}$, $Y^{3+}$, $La^{3+}$, $Cu^{2+}$, $Zn^{2+}$, $Cd^{2+}$, $Ag^+$, $Au^+$, $H^+$, $NH_4^+$, and $NR_4^+$ where R is an alkyl, aryl, alkylaryl, or arylalkyl group.

The cationic modifiers are generally added to unmodified Na-ETS-10 in the form of a salt or an acid. The anionic counter-ion associated with the cationic modifier is not specifically defined, provided that it does not adversely affect the modification (i.e. cation exchange) reactions. Suitable anions include but are not limited to acetate, carboxylate, benzoate, bromate, chlorate, perchlorate, chorite, citrate, nitrate, nitrite, sulfates, halide (F, Cl, Br, I) and mixtures thereof. Suitable acids include inorganic and organic acids, with inorganic acids being preferred.

The Na-ETS-10 zeolite may be cation exchanged by any of the known conventional techniques. For example, a Na-ETS-10 zeolite may be cation exchanged by treatment with a cationic modifier in a stirred aqueous solution. After the cation exchange reactions are carried out, the resulting modified ETS-10 zeolites can be treated in any conventional manner, including but not limiting to washing and drying steps as well as calcination and granulation steps.

In an aspect of the invention, the modified ETS-10 zeolite is an "as-prepared" ETS-10 zeolite that has been structurally modified. Either or both of Ti and Si may be substituted by an octahedral metal and tetrahedral metal, respectively.

In an aspect of the invention, titanium is partially substituted by an octahedral metal selected from the group consisting of but not limited to arsenic, cobalt, chromium, copper, iron, germanium, hafnium, magnesium, manganese, molybdenum, niobium, nickel, antimony, tin, uranium, vanadium, yttrium, zinc, zirconium, lanthanum, an actinide, a lanthanide and mixtures thereof.

In an aspect of the invention, silicon is partially substituted by a tetrahedral metal selected from the group consisting of but not limited to aluminum, arsenic, bismuth, boron, beryllium, cobalt, chromium, copper, iron, gallium, germanium, indium, lead, magnesium, manganese, molybdenum, niobium, nickel, antimony, tin, titanium, vanadium, tungsten, zinc and mixtures thereof.

Structurally modified ETS-10 zeolites have a composition that in some aspects of the invention may be represented by the following formula:

$$a(1.0\pm0.25)M_{2/n}O:AO_\alpha:dBO_\beta:0\text{-}100H_2O,$$

where M is at least one cation of valence n; $\alpha$ is ½ the valence of A; $\beta$ is ½ the valence of B; d is 2-100; a is equal to ½ the charge provided by the total of A and B; A is octahedrally coordinated titanium alone or a mixture of octahedrally coordinated titanium and another octahedrally coordinated metal; B is silicon alone or a mixture of silicon and another tetrahedrally coordinated metal; provided that when A is only titanium, B cannot be only silicon and that when B is only Si, A cannot be only Ti.

In an aspect of the invention, structurally modified ETS-10 zeolites are crystalline molecular sieves having a pore size of at least 8 Angstrom units.

In an aspect of the invention, A is titanium alone or a mixture of titanium and another metal selected from the group consisting of but not limited to arsenic, cobalt, chromium, copper, iron, germanium, hafnium, magnesium, manganese, molybdenum, niobium, nickel, antimony, tin, uranium, vanadium, yttrium, zinc, zirconium, lanthanum, an actinide, a lanthanide and mixtures thereof.

In an aspect of the invention, B is silicon alone or a mixture of silicon and another metal selected from the group consisting of but not limited to aluminum, arsenic, bismuth, boron, beryllium, cobalt, chromium, copper, iron, gallium, germanium, indium, lead, magnesium, manganese, molybdenum, niobium, nickel, antimony, tin, titanium, vanadium, tungsten, zinc, and mixtures thereof.

The Na-ETS-10 zeolite may be structurally modified by any of the known techniques that are described in for example, U.S. Pat. Nos. 5,208,006 and 5,244,650, which are incorporated herein by reference. For example, the structurally modified molecular sieves may be prepared from a reaction mixture containing a source of titanium or titanium and at least one other metal capable of being octahedrally coordinated, and also containing a source of silicon or silicon and at least one other metal capable of being tetrahedrally coordinated in the framework structure, a source of alkalinity such as an alkali or alkaline earth metal hydroxide, water and, optionally, an alkali or alkaline earth metal salt.

In an aspect of the invention, a structurally modified ETS-10 zeolite is prepared from a reaction mixture having a composition in terms of molar ratios of:

B/A=from about 1 to about 200
$H_2O$/B=from about 1 to about 100
$M_n$/A=from about 1 to about 100 wherein M indicates the cations of valence n derived from the alkali or earth metal and metal salts, and A and B are defined as above.

In an aspect of the invention, a structurally modified ETS-10 zeolite is prepared from a reaction mixture having a composition in terms of molar ratios of:

$SiO_2$/Al=from about 1 to about 200
$SiO_2$/Ti=from about 2 to about 20
$H_2O$/$SiO_2$=from about 2 to about 100
$M_n$/$SiO_2$=from about 0.1 to about 20 wherein M indicates the cations of valence n derived from the alkali or earth metal and metal salts. Such, aluminum modified ETS-10 zeolites have been dubbed, ETAS-10 zeolites (see U.S. Pat. No. 5,244,650).

The Na-ETS-10 may also be modified by adding a source of metal which is capable of being octahedrally or tetrahedrally coordinated within the titanosilicate framework structure, to a previously prepared Na-ETS-10. By way of non-limiting example, a source of aluminum (e.g. $AlCl_3.6H_2O$) may be added to previously prepared Na-ETS-10 to exchange silicon for aluminum, which is described in U.S. Pat. No. 5,244,650 (see especially Examples 1-7) that is incorporated herein by reference. The source of metal which is capable of being octahedrally or tetrahedrally coordinated in the framework structure may be stirred and heated with the as-prepared Na-ETS-10 in the presence or absence of solvent or water to effect Ti and/or Si substitution. Other well known methods for mixing zeolites with additive compounds may also be used.

The current invention also contemplates modifications that remove (i.e. extract) a portion of the titanium from an "as-prepared" Na-ETS-10, provided that the framework structure of the Na-ETS-10 remains intact and that the zeolite remains selective for $CO_2$ adsorption. Methods to remove titanium from an ETS-10 type zeolite are described in U.S. Pat. No. 5,906,954 and include treating the zeolite with complexing agents such as but not limited to ethylene diamine tetraacetic acid, oxalic acid and citric acid, amines, hydroxyl carboxylates and beta diketones.

In an aspect of the invention, the modified ETS-10 zeolite is an "as-prepared" ETS-10 zeolite that has been both cationically modified and structurally modified.

The ETS-10 zeolites used in the current invention can be used in a wide variety of forms. For example, the modified ETS-10 zeolites may be in the form of a powder, a granule, an extrudate or other particulate form suitable for use in an adsorbent bed. The ETS-10 zeolites can be mixed with other components prior to use as an adsorbent, most typically in an adsorbent bed. For example, natural or synthetic clays, aluminophosphates, agglomerates of clay and silica, silica or other metal oxides, and mixtures thereof may be added to the ETS-10 zeolites.

The ETS-10 zeolites can be used with any cycle swing adsorption process for the separation/enrichment of binary or multi-component mixtures of carbon dioxide and paraffins. For example, pressure swing adsorption (PSA) processes including vacuum swing adsorption (VSA), thermal swing adsorption (TSA) processes and combinations thereof can be used. The cycle swing adsorption process can comprise multiple adsorption and regeneration steps as well as purging and depressurization steps. Pressure swing and temperature swing processes are well known in the art.

Pressure swing adsorption can include, in addition to adsorption and regeneration steps: purge steps, venting steps, pressure equalization steps, evacuation steps, blowdown steps. Steps can be carried out in concurrent, alternating or sequential fashion and gas flows can be continuous, discontinuous, co-current and counter-current, all of which are well known in the art. In a PSA process one or more adsorbent beds can be arranged in series or in parallel. Some non-limiting examples of PSA processes are described in *Adsorption, Gas Separation* in the Kirk-Othmer Encyclopedia of Chemical Technology, Copyright John Wiley & Sons, Inc. vol 1, pgs 642-647 and references cited therein as well as in U.S. Pat. Nos. 3,430,418; 4,589,888; 6,293,999; 6,197,092 and 6,497,750 all of which are incorporated herein by reference.

Temperature swing adsorption (TSA) is described in Adsorption, Gas Separation in the Kirk-Othmer Encyclopedia of Chemical Technology, Copyright John Wiley & Sons, Inc. vol 1, pgs 636-642 and references cited therein all of which are incorporated herein by reference.

In an aspect of the present invention, at least one ETS-10 containing adsorbent bed is used in a pressure swing adsorption process to separate/enrich gaseous mixtures of paraffins and carbon dioxide, preferably for the separation of methane and/or ethane from, or the enrichment of methane and/or ethane within, a gaseous mixture containing methane and/or ethane as well as carbon dioxide.

In an aspect of the present invention, at least one ETS-10 containing adsorbent bed is used in a pressure swing adsorption process carried out at ambient temperatures, to separate/enrich gaseous mixtures of paraffins and carbon dioxide, preferably the separation of methane and/or ethane from, or the enrichment of methane and/or ethane within, a gaseous mixture containing methane and/or ethane as well as carbon dioxide.

In another aspect of the invention, at least one ETS-10 containing adsorbent bed is used in a combined pressure swing/temperature swing adsorption process to separate/enrich gaseous mixtures of paraffins and carbon dioxide, preferably the separation of methane and/or ethane from, or the enrichment of methane and/or ethane within, a gaseous mixture containing methane and/or ethane as well as carbon dioxide.

The pressures at which adsorption and regeneration steps are carried out are not specifically defined, and depend on a number of factors such as but not limited to the temperature used, the type of cation used to modify the Na-ETS-10 zeolite (when optional cationic modification is carried out), the type of structural modification of the Na-ETS-10 zeolite (when optional structural modification is carried out), and the nature of the paraffin and/or acidic gas to be separated/enriched. Typically, the range of absolute pressures used during the adsorption step can be from about 10 kPa to about 2,000 kPa. Generally, the range of pressures used during the release of adsorbate (i.e. during the regeneration step) can be from about 0.01 kPa to about 150 kPa.

The temperatures at which the adsorption over the ETS-10 zeolite takes place will depend on a number of factors, such as but not limited to the particular paraffin and/or acidic gas to be separated/enriched, the type of cation used to modify the Na-ETS-10 zeolite (when optional cationic modification is carried out), the type of structural modification of the Na-ETS-10 zeolite (when optional structural modification is carried out), and the pressure at which adsorption is to be carried out. In general, the adsorption step can be carried out at from ambient temperatures to above about 100° C., provided that the temperatures do not exceed temperatures at which chemical reaction/decomposition of the paraffins and/or carbon dioxide, takes place. Temperatures that favor adsorption and desorption over the pressure range of about 0.1 kPa to about 1000 kPa are generally preferred. For reasons of economics, in one aspect of the current invention, it is desirable to use ambient temperatures during both the adsorption and desorption steps.

In an aspect of the current invention, a cationically modified ETS-10 zeolite has a superior pressure swing capacity for carbon dioxide and methane adsorption/desorption, in the pressure range of about 1 kPa to about 100 kPa, than an unmodified Na-ETS-10 zeolite.

In an aspect of the current invention, a cationically modified ETS-10 zeolite has a superior pressure swing capacity for carbon dioxide and ethane adsorption/desorption, in the pressure range of about 1 kPa to about 100 kPa, than an unmodified Na-ETS-10 zeolite.

In an aspect of the current invention, a cationically modified ETS-10 zeolite has a pressure swing capacity of at least about 0.5 mmol/g, preferably at least about 1.0 mmol/g for carbon dioxide, in the pressure range of about 1 kPa to about 100 kPa, at a temperature of about 25° C.

In an aspect of the current invention, a modified and/or unmodified ETS-10 zeolite is used to selectively adsorb carbon dioxide from a gaseous feedstream minimally containing ethane and carbon dioxide, to produce an adsorbed phase enriched in carbon dioxide and a non-adsorbed phase enriched in ethane. Desorption from the modified or unmodified ETS-10 zeolite occurs at a pressure which is lower than the adsorption pressure, and a gaseous mixture enriched in carbon dioxide may be recovered for use as product or again enriched by further treatment with modified and/or unmodified ETS-10 zeolite. Likewise, a gaseous mixture enriched in ethane may be recovered for use as product or again enriched by further treatment with modified and/or unmodified ETS-10. The feedstream may optionally contain other gases such as carbon monoxide, oxygen, nitrogen, hydrogen, unsaturated hydrocarbons and the like. Components such as hydrogen sulfide may also be present in the feedstream and are preferably removed prior to contact with the adsorbent. Methods to remove hydrogen, hydrogen sulfide, carbon monoxide etc. are well known in the art.

In the current invention, the modified or unmodified ETS-10 zeolite can be used in a pressure swing adsorption (PSA) process that is upstream from a hydrocracking or catalytic cracking unit. A hydrocarbon cracking unit typically employs hydrothermal pyrolysis or high temperature catalytic processes to crack feedstocks such as but not limited to natural gas, naphtha, gas oil, hydrocarbons and paraffins for the production of light olefins such as ethylene and propylene. Preferred cracking processes include stream and catalytic cracking of ethane to form ethylene; for example, a conventional ethane hydrocracking plant.

The methods and processes of the current invention can be used in a variety of petroleum refining and petrochemical operations where the separation of paraffins such as methane or ethane from carbon dioxide is desired. For example, the current process can be used to perform a rough separation of carbon dioxide from paraffins prior to further removal of carbon dioxide with a conventional liquid extraction unit or alternatively to perform a final purification or finishing step after a rough cut liquid extraction of carbon dioxide from paraffins using conventional liquid extraction technologies, such as for example amine based extractants (for a recent example in which a CTS-1 titanosilicate adsorbent is combined with a traditional amine solvent scrubber to purify natural gas, see U.S. Pat. No. 7,314,503 to Syntroleum).

In the present invention, modified or unmodified ETS-10 zeolites can be used in one or more PSA beds, upstream or downstream of a conventional $CO_2$ scrubber unit such as for example an amine based liquid extraction unit (for an early reference on solvent extraction systems see U.S. Pat. No. 2,860,030).

Without wishing to be bound by any single theory, use of PSA units containing modified or unmodified ETS-10 zeolites can augment the separation performance of a scrubber unit by increasing the proportion of paraffins in a mixture of paraffins and carbon dioxide. As a result, the investment and energy requirements for a conventional $CO_2$ scrubber, may correspondingly be reduced.

EXAMPLES

Unmodified ("as-prepared") Na-ETS-10 Zeolites

Unmodified ETS-10 was synthesized hydrothermally as described in U.S. Pat. No. 5,011,591. A typical preparation involved thorough mixing of 50 g of sodium silicate (28.8% $SiO_2$, 9.14% $Na_2O$ obtained from Fisher Scientific), 2.3 g of sodium hydroxide (97$^+$% NaOH, obtained from Fisher Scientific), 3.8 g of anhydrous KF (Fisher Scientific), 4 g of HCl (1M aqueous solution), and 16.3 g of $TiCl_3$ solution (20 wt. % solution in 2N Hydrochloric Acid, from Fisher Scientific). The mixture was stirred in a blender for 1 h and then placed in a 125 mL sealed autoclave (by PARR Instruments) at 215° C. for 64 h. This gave a resultant material that was washed with de-ionized water and dried in an oven at 100° C. The material can be ground into powders or extruded into pellets ranging from 10 to 100 mesh.

Preparation of Modified ETS-10 Zeolites by Cation Exchange

Cation-exchange was carried out by exposing Na-ETS-10 material prepared as above (a less than 100 mesh powder) to an excess of aqueous ionic solution at 100° C. with stirring for 24 h. The aqueous ionic solutions added were for example, an aqueous solution of $BaCl_2$. The exchanged materials were washed with de-ionized water and dried at 100° C. A person skilled in the art will recognize that other cations can be added to the ETS-10 material in a similar fashion.

Mixed cationic forms of ETS-10 including Ba/H forms were prepared by exposing Na-ETS-10 powder to 1 meq/g of an aqueous solution of $BaCl_2$ at 100° C. with stirring for 24 h. This provided partially exchanged materials that were then exposed to an HCl solution maintained at a pH of 2 for 8 h at 20° C. The final products were washed with de-ionized water and dried at 100° C.

Adsorption Isotherms for Carbon Dioxide ($CO_2$), Methane ($CH_4$) and Ethane ($C_2H_6$)

Carbon dioxide, methane, and ethane adsorption isotherms at 25° C. and up to 1 bar were measured in an Autosorb-1 MP volumetric system from Quantachrome Instruments, Boynton Beach, Fla. This system is equipped with low pressure range transducers (0-1 Torr) that allow the direct measurements of very low pressure points of the adsorption isotherms, including those corresponding to the initial linear region (Henry's law regime) of carbon dioxide isotherms. Samples were generally dried at 200° C. for 6 h under vacuum before the adsorption experiments.

Henry's law constants (K) were determined directly from the linear region of the isotherms and were also calculated from the Langmuir equation applied to the low pressure adsorption data (for details on how to determine K, see the theoretical background in the *J. Chem. Eng. Data*. 2005, 50, p 843 by Al-Baghli et al.). Both methods for the determination of the Henry's law constants gave equivalent results. The limiting selectivity ($\alpha$) of the adsorbent for the gas A over the gas B is calculated as the ratio of their respective Henry's law constants:

$$\alpha(A/B) = \frac{K_A}{K_B}.$$

In the current specification, the pressure swing capacity of a given adsorbent is defined as the adsorption capacity between pressures of 1-100 kPa. A partial pressure of 1 kPa was selected to allow a common basis of comparison and because highly rectangular isotherms tend to hold a significant portion of their capacity below 1 kPa. Working capacity percentage is normalized with respect to the total adsorption at 1 bar (i.e. 100 kPa).

FIG. 1 depicts carbon dioxide, ethane and methane adsorption isotherms for three different cationic forms of ETS-10: Na—, Ba—, and Ba/H-ETS-10 (1 meq Ba). The adsorption isotherms are shown from 0 to 100 kPa (FIGS. 1a-1d) and in expanded form 0 to 1 kPa (FIGS. 1d-1f). Isotherms for Na-ETS-10 (FIGS. 1a and 1d) follow the capacity sequence $CO_2 > C_2H_6 > CH_4$. Carbon dioxide and ethane isotherms for Ba-ETS-10 (FIGS. 1b and 1e) are less rectangular than for Na-ETS-10. For Ba/H-ETS-10 (FIGS. 1c and 1f), carbon dioxide and ethane isotherms are even less rectangular than for fully exchanged Ba-ETS-10.

The Henry's constants for the adsorption of carbon dioxide, ethane, and methane on ETS-10 materials decrease with cation exchange in the order Na>Ba>Ba/H, but the limiting selectivity of $CO_2$ over ethane and methane does not undergo appreciable changes (Table 1). The swing capacity of $CO_2$ for ETS-10 materials increases in the order Na<Ba<Ba/H (Table 2). More than 90% of the total $CO_2$ capacity for Ba/H-ETS-10 is observed inside the gas pressure region of 1-100 kPa, while this material still demonstrates $CO_2$ selectivity over ethane ($\alpha$=8.8) and high selectivity over methane ($\alpha$=150). The data shows that Ba/H-ETS-10 (1 meq Ba) would be an effective adsorbent for the PSA separation of $CO_2$ from light paraffins under certain conditions (i.e. Ba/H-ETS-10 (1 meq Ba) would be an effective adsorbent for the PSA enrichment of methane and/or ethane in a mixture of carbon dioxide and the same). Fully exchanged Ba-ETS-10 also demonstrates a large $CO_2$ swing capacity, and would be useful to effect the PSA separation of $CO_2$ from light paraffins (i.e. the PSA enrichment of methane and/or ethane in a mixture of carbon dioxide and the same) under appropriate conditions.

TABLE 1

Henry's Law Constants (K) and Limiting Selectivity ($\alpha$) for the Adsorption of Carbon Dioxide, Ethane and Methane on Various Titanosilicate Molecular Sieves

| | K [mmol · g$^{-1}$ · kPa$^{-1}$] | | | | $\alpha$($CO_2$/ |
|---|---|---|---|---|---|
| | $CO_2$ | $C_2H_6$ | $CH_4$ | $\alpha$($CO_2$/$C_2H_6$) | $CH_4$) |
| Na-ETS-10 | 5.2 | 9.5 · 10$^{-1}$ | 1.6 · 10$^{-2}$ | 5.5 | 3.2 · 10$^2$ |
| Ba-ETS-10 | 2.1 | 6.2 · 10$^{-1}$ | 1.2 · 10$^{-2}$ | 3.4 | 1.7 · 10$^2$ |
| Ba/H-ETS-10[a] | 1.2 | 1.4 · 10$^{-1}$ | 7.8 · 10$^{-3}$ | 8.8 | 1.5 · 10$^2$ |

[a] 1 meq Ba$^{2+}$

TABLE 2

Swing Capacity (1-100 kPa) for the Adsorption of Carbon Dioxide, Ethane and Methane on Various Titanosilicate Molecular Sieves.

| | $CO_2$ mmol/g | % | $C_2H_6$ mmol/g | % | $CH_4$ mmol/g | % |
|---|---|---|---|---|---|---|
| Na-ETS-10 | 1.14 | 57 | 0.82 | 61 | 0.76 | 98 |
| Ba-ETS-10 | 1.78 | 77 | 1.26 | 72 | 0.64 | 98 |
| Ba/H-ETS-10[a] | 1.88 | 91 | 1.14 | 90 | 0.51 | 99 |

[a] 1 meq $Ba^{2+}$

What is claimed is:

1. A process for increasing the proportion of at least one light paraffin in a mixture comprising carbon dioxide and said at least one light paraffin, wherein said process comprises passing said mixture over an adsorbent, wherein said adsorbent comprises an as-prepared and/or modified ETS-10 zeolite, said adsorbent selectively adsorbs carbon dioxide from said mixture, and said at least one paraffin comprises methane, ethane or a mixture thereof.

2. The process of claim 1, wherein said at least one light paraffin comprises more than 50 weight percent of ethane.

3. The process of claim 1, wherein said at least one light paraffin comprises more than 50 weight percent of methane.

4. The process of claim 1, 2, or 3, wherein said modified ETS-10 zeolite comprises an as-prepared Na-ETS-10 zeolite which has been modified by cation exchange with one or more than one mono-, di- or tri-valent metal cation, a proton or mixtures thereof.

5. The process according to claim 4 wherein said process is a pressure swing adsorption process.

6. The process according to claim 1, 2, or 3, wherein said process is a pressure swing adsorption process.

7. A pressure swing adsorption process for increasing the proportion of at least one light paraffin in a gaseous mixture comprising carbon dioxide and said at least one light paraffin, wherein said process comprises:

i) passing said mixture through at least one adsorption bed containing an adsorbent comprising an as-prepared and/or modified ETS-10 zeolite, at a pressure at which said adsorbent selectively adsorbs carbon dioxide from said gaseous mixture to provide a stream enriched in said at least one light paraffin;

ii) reducing the pressure in said at least one adsorption bed to a pressure at which said adsorbent releases adsorbed carbon dioxide to provide a stream enriched in carbon dioxide; and wherein said at least one light paraffin comprises methane, ethane or a mixture thereof.

8. A process comprising:

i) passing a mixture comprising carbon dioxide and ethane through at least one adsorbent bed containing an adsorbent comprising an as-prepared and/or modified ETS-10 zeolite, wherein said as-prepared and/or modified ETS-10 zeolite selectively adsorbs carbon dioxide from said mixture to provide a product stream enriched in said ethane; and ii) cracking said ethane in said product stream in a hydrocarbons cracking unit.

9. A process for increasing the proportion of at least one light paraffin in a mixture comprising carbon dioxide and said at least one light paraffin, wherein said process comprises:

i) passing said mixture over an adsorbent, wherein said adsorbent comprises an as-prepared and/or modified ETS-10 zeolite, and wherein said adsorbent selectively adsorbs carbon dioxide from said mixture; and ii) passing said mixture through an amine based liquid extraction unit, wherein said extraction unit selectively extracts carbon dioxide from said mixture;

and provided that said at least one light paraffin comprises more than 50 weight percent of ethane.

* * * * *